United States Patent [19]
Dunges

[11] 3,949,806
[45] Apr. 13, 1976

[54] METHOD AND APPARATUS FOR REFLUXATION IN MICROLITER SCALE

[76] Inventor: Wolfgang Dunges, Rilkeallee 14, 65 Mainz-31, Germany

[22] Filed: Apr. 8, 1974

[21] Appl. No.: 459,095

[52] U.S. Cl. .................. 165/2; 55/67; 55/197; 210/31 C; 210/198 C
[51] Int. Cl.[2] .......................... F25B 13/00
[58] Field of Search......... 210/31 C, 198 C; 55/197, 55/67; 23/232 E; 259/155, DIG. 18; 165/2

[56] References Cited
UNITED STATES PATENTS

| | | | |
|---|---|---|---|
| 3,324,628 | 6/1967 | Natelson | 55/67 |
| 3,357,157 | 12/1967 | O'Donnell | 55/197 |
| 3,369,874 | 2/1968 | Wilhelm | 55/197 |
| 3,578,757 | 5/1971 | Samuilov | 55/197 |
| 3,617,557 | 11/1971 | Giltrow | 210/31 C |

*Primary Examiner*—Charles J. Myhre
*Assistant Examiner*—Daniel J. O'Connor
*Attorney, Agent, or Firm*—Littlepage, Quaintance, Murphy & Dobyns

[57] ABSTRACT

Refluxation of liquids in microliter quantities of as little as 5 $\mu l$ are performed in an apparatus consisting of a holder which holds the microvessels such that the lower part thereof is immersed in a heating bath, while the holder is being continuously vibrated. The upper part of the microvessels may be cooled at the same time the lower part is heated. The process is particularly suited for performing two phase micro-reactions.

8 Claims, 1 Drawing Figure

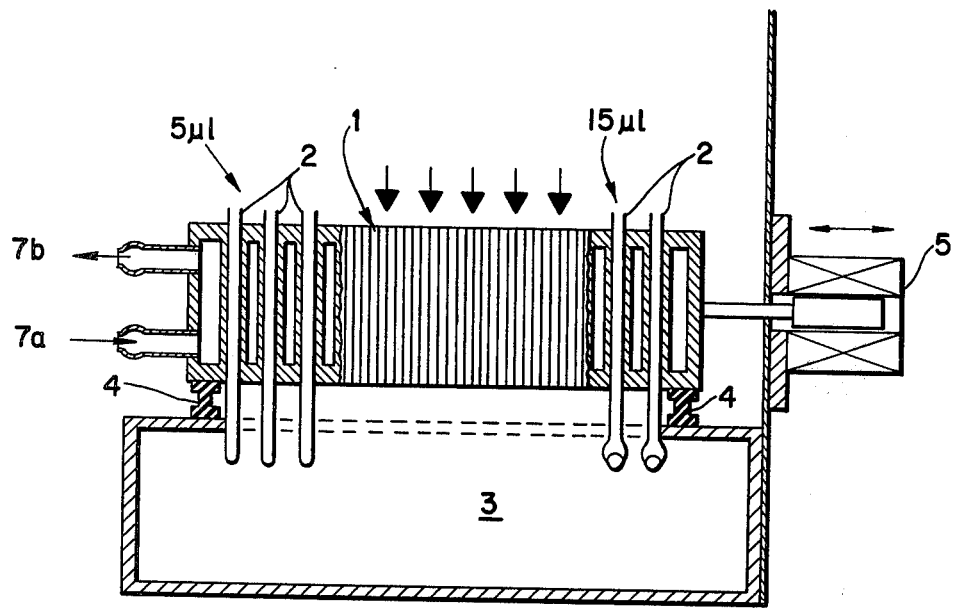

METHOD AND APPARATUS FOR REFLUXATION IN MICROLITER SCALE

The invention relates to a process for refluxing liquids in microliter scale. The invention also relates to an apparatus for performing such refluxations. The process is characterized in that the microvessels in which the liquids are refluxed are kept in continuous vibration during the said refluxation.

Up to now refluxation of liquid is restricted to amounts above 30 to 50 μl, mainly because of the disturbing influences of surface forces on liquids in these small volumes.

It has now been surprisingly discovered that refluxations in microliter scale, i.e., refluxations of quantities of as little as 5 μl can be performed smoothly, without essential loss of liquid. By the process of the invention even micro-reactions, e.g. two phase ester formation using a fatty acid, an alkylating agent dissolved in an organic solvent, and solid potassium carbonate can be performed successfully, because the reactants become thoroughly mixed. Since the lower part of the reaction vessels is heated in a heating bath, such as an hot air bath, while being continuously vibrated, the formation of droplets at the cooler upper areas of the vessel is suppressed, and a constant backflow is achieved. In a preferred embodiment of the invention the upper part of the reaction vessels is cooled, e.g., by cooling the device to which the microvessels are attached.

A suitable apparatus for performing the refluxations according to the invention is described herein after with reference to the attached drawings. The apparatus consists of a holder 1 carrying the microvessels 2 (tubes or flasks etc.), each microvessel 2 having an upper part or portion 11 and a lower portion 12 which is immersed into a heating medium 6 contained on a heating bath 3. The heating medium 6 can be any suitable medium, such as hot air or oil etc. The holder 1 is connected to a vibrator 5, which may be any suitable vibrating device, such as an electrical oscillating motor, a magnetic, pneumatic, hydraulic or mechanic vibrator etc.. The holder 1 may rest on a resilient support 4. The holder 1 may consist of a block 8 of light metal having vertical bores 9 for receiving the microvessels 2 by means of O-rings, as well as channels 10 for flowing a suitable cooling fluid through the said holder. The cooling fluid is entering the holder at 7a and is leaving it at 7b. In the drawing there are shown micro tubes of 5 μl content and micro flasks of 15 μl content.

The following example illustrates the process of the invention:

EXAMPLE

Gas Chromatography

Sharp and symmetrical peaks are a prerequisite for an optimum gas chromatographic analysis. With many compounds satisfactory analyses are therefore impossible in the submicrogram range because of the strong tailing of their peaks, in order to avoid this phenomenon organic acids, e.g. are alkylated. Sharp peaks result even in the nanogram range. The free acids are dissolved in an organic solvent with an excess of the alkylating reagent. The solution is refluxed together with solid $K_2CO_3$. As water is excluded from the reaction mixture the solution can be rejected without further steps directly into the gas chromatograph.

Through the application of the microrefluxer the volume of the reaction solution can be restricted to 5 microliters. Thus the total injection of the whole analytical solution is feasible. The sensitivity of the gas chromatograph is thus used to its full extent. As several different Alkylating reagents can be used different derivatives from one starting compound can be obtained.

What is claimed is:

1. In a method of refluxing a liquid in a vessel of less than 50 μl content wherein the lower part of the vessel is heated while the upper part of the vessel is cooled, the improvement comprising continuously vibrating said vessel during the time of refluxation whereby the formation of droplets is suppressed in the upper portion of said vessel.

2. An apparatus for refluxing microliter quantities of liquid comprising a vessel of less than 50μl content having an upper portion and a lower portion, and means for suppressing the formation of liquid droplets at the upper portion of the vessel comprising:
   a holder for receiving said vessel and
   a vibrating device connected to the holder for vibrating the holder and the vessel such that the formation of droplets is suppressed in the upper portion of said vessel and a constant back flow of liquid to said lower portion of the vessel is achieved.

3. An apparatus as in claim 2, wherein said holder contains channels for flowing a cooling liquid therethrough.

4. An apparatus as in claim 2, wherein said heating bath consists of a hot air bath.

5. An apparatus as in claim 2, wherein said holder consists of a hollow light metal block having vertical bores for receiving the said vessels by means of O-rings.

6. In the practice of refluxing microliter quantities of a liquid in a vessel of less than 50μl content, said vessel having an upper portion and a lower portion, the improved method of suppressing the formation of liquid droplets at said upper portion of the vessel and providing a constant back flow of liquid to said lower portion of the vessel comprising the step of continuously vibrating said vessel during the time of refluxation such that the formation of droplets is suppressed in the upper portion of said vessel.

7. In the practice of refluxing microliter quantities of a liquid in a vessel of less than 50μl content, said vessel having an upper portion and a lower portion, said practice comprising the steps of supporting said upper portion of the vessel in a holder containing channels for flowing a cooling liquid there through, positioning said holder over a heating bath such that said lower portion of the vessel is immersed in a heating medium, placing a microliter quantity of said liquid to be refluxed in the vessel, and flowing a cooling liquid through said channels in said holder, the improved method of suppressing the formation of liquid droplets at said upper portion of the vessel and providing a constant back flow of liquid to said lower portion of the vessel comprising the step of continuously vibrating said holder and said vessel during the time of refluxation.

8. An apparatus for refluxing microliter quantities of liquid comprising:
   a heating bath containing a heating medium,
   a vessel of less than 50 microliters content containing a liquid to be refluxed, said vessel having an upper portion and a lower portion, the lower portion of said vessel being immersed in said heating medium, a holder positioned above said heating bath for receiving said upper portion of said vessel, the holder comprising:

a block of light metal, a vertical bore in said block for receiving said vessel, a channel in said block through which a suitable cooling fluid can flow, means for introducing the cooling fluid and means for withdrawing the cooling fluid, a resilient support for supporting said holder with said vessel over said bath, and a vibrating device connected to said holder and to said heating bath for vibrating said holder and said vessel such that the formation of droplets at said upper portion of said vessel is suppressed and a constant back flow of said liquid is achieved.

* * * * *

UNITED STATES PATENT OFFICE
CERTIFICATE OF CORRECTION

Patent No. 3,949,806          Dated April 13, 1976

Inventor(s) Wolfgang Dunges          Page 1 of 2

It is certified that error appears in the above-identified patent and that said Letters Patent are hereby corrected as shown below:

The amended drawing as shown below should be substituted therefor:

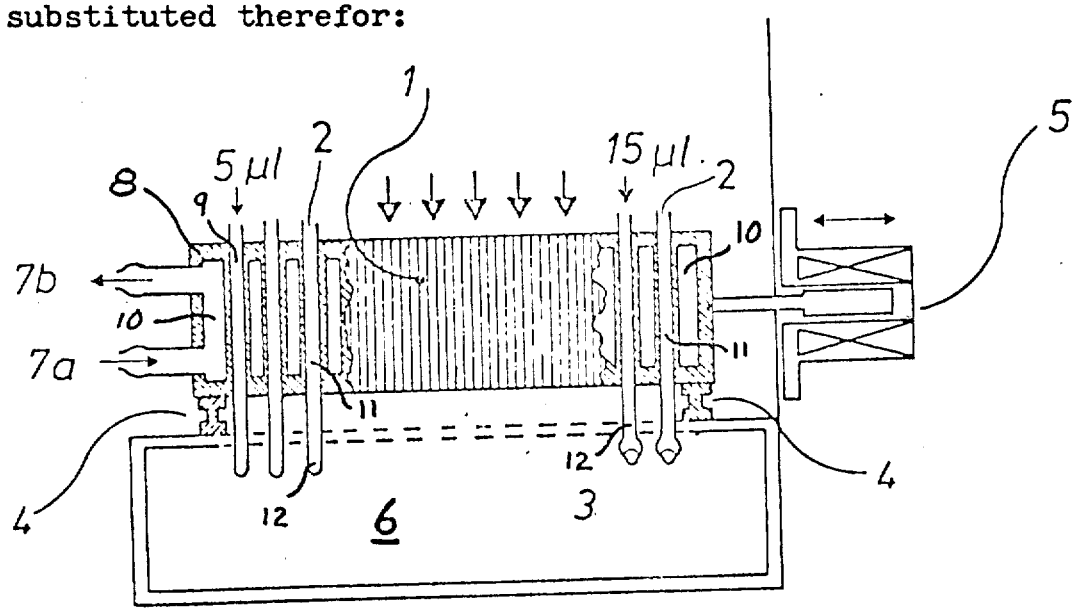

UNITED STATES PATENT AND TRADEMARK OFFICE
CERTIFICATE OF CORRECTION

PATENT NO. : 3,949,806
DATED : April 13, 1976
INVENTOR(S) : Wolfgang Dunges

It is certified that error appears in the above-identified patent and that said Letters Patent are hereby corrected as shown below:

Column 1, line 37, delete "on" and insert --in--;

line 67, delete "rejected" and insert --injected--.

Signed and Sealed this

Twenty-sixth Day of October 1976

[SEAL]

*Attest:*

RUTH C. MASON
*Attesting Officer*

C. MARSHALL DANN
*Commissioner of Patents and Trademarks*